United States Patent [19]

Reid

[11] 4,101,777
[45] * Jul. 18, 1978

[54] FLUID PURIFICATION DEVICE AND ULTRAVIOLET LAMP THEREFOR

[76] Inventor: William P. Reid, 3200 E. 29th St., Long Beach, Calif. 90806

[*] Notice: The portion of the term of this patent subsequent to Dec. 2, 1992, has been disclaimed.

[21] Appl. No.: 611,080

[22] Filed: Sep. 8, 1975

Related U.S. Application Data

[63] Continuation-in-part of Ser. No. 490,238, Jul. 22, 1974, Pat. No. 3,923,663.

[51] Int. Cl.² ............................................. G01N 21/26
[52] U.S. Cl. ................................ 250/436; 250/432 R; 210/251
[58] Field of Search ................. 210/251, 222, 223, 243, 210/169, 443; 119/5; 250/435, 436, 437, 438; 21/54 R, 102 R, DIG. 2

[56] References Cited

U.S. PATENT DOCUMENTS

| 2,501,290 | 3/1950 | Pequignot | 250/437 X |
|---|---|---|---|
| 2,563,786 | 8/1951 | James | 210/444 X |
| 2,648,774 | 8/1953 | Whitlock | 250/435 |
| 3,413,465 | 11/1968 | Harrison et al. | 250/437 X |
| 3,511,776 | 5/1970 | Avampato | 210/222 |
| 3,551,091 | 12/1970 | Veloz | 250/436 X |
| 3,602,712 | 8/1971 | Mann | 250/437 |
| 3,680,705 | 8/1972 | Happer et al. | 210/222 |
| 3,683,177 | 8/1972 | Veloz | 119/5 |
| 3,923,663 | 12/1975 | Reid | 210/251 |

Primary Examiner—Charles N. Hart
Assistant Examiner—Richard W. Burks
Attorney, Agent, or Firm—Paul A. Weilein

[57] ABSTRACT

A unitary device for purifying water and other fluids embodying an annular filter surrounding an elongate tube which in turn surrounds and cooperates with an elongate ultraviolet lamp to form a flow channel for fluid to be irradiated. Fluid passing through the filter is conveyed through the flow channel along the length of the lamp to effect sterilization. The lamp is encased in a film of material having non-stick characteristics with respect to the fluid being treated, such as fluorinated ethylene propylene, to prevent buildup of scale and other contamination on the surface of the lamp which would otherwise reduce transmission of ultraviolet rays to the fluid. The lamp assembly is constructed as a replaceable removable unit which is adapted to be mounted in reversed endwise position to accommodate the device for different types of installations.

10 Claims, 5 Drawing Figures

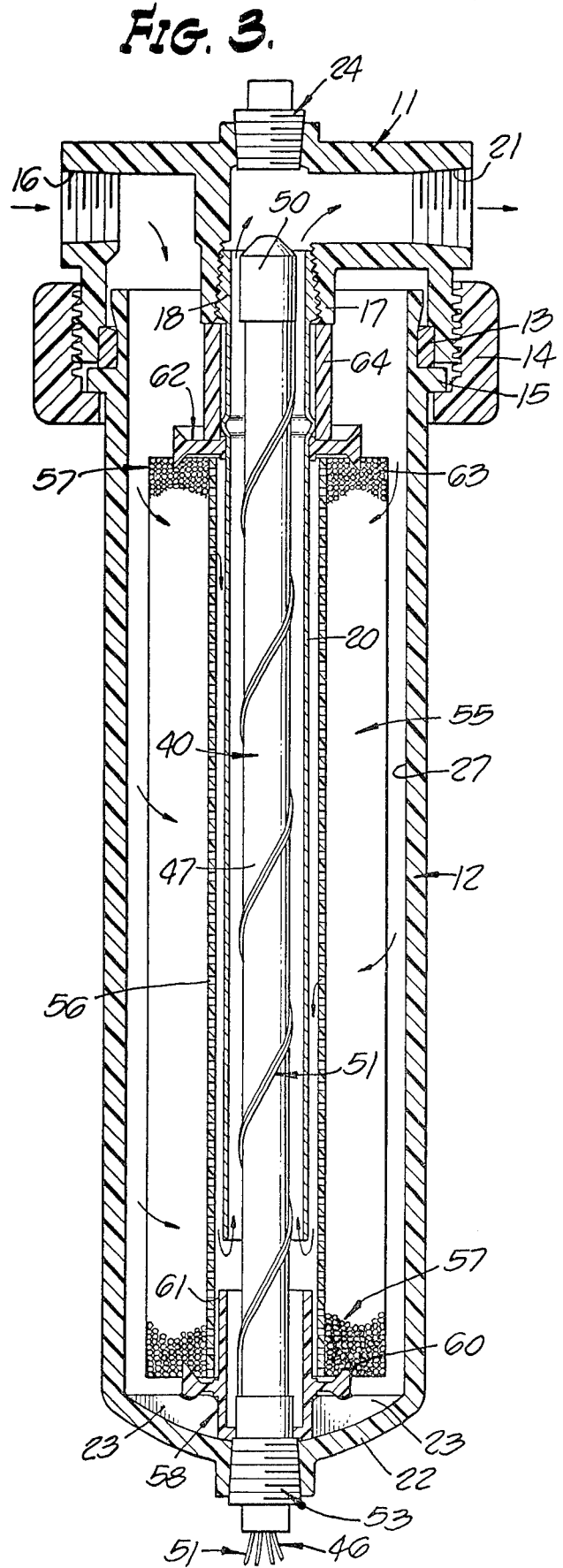
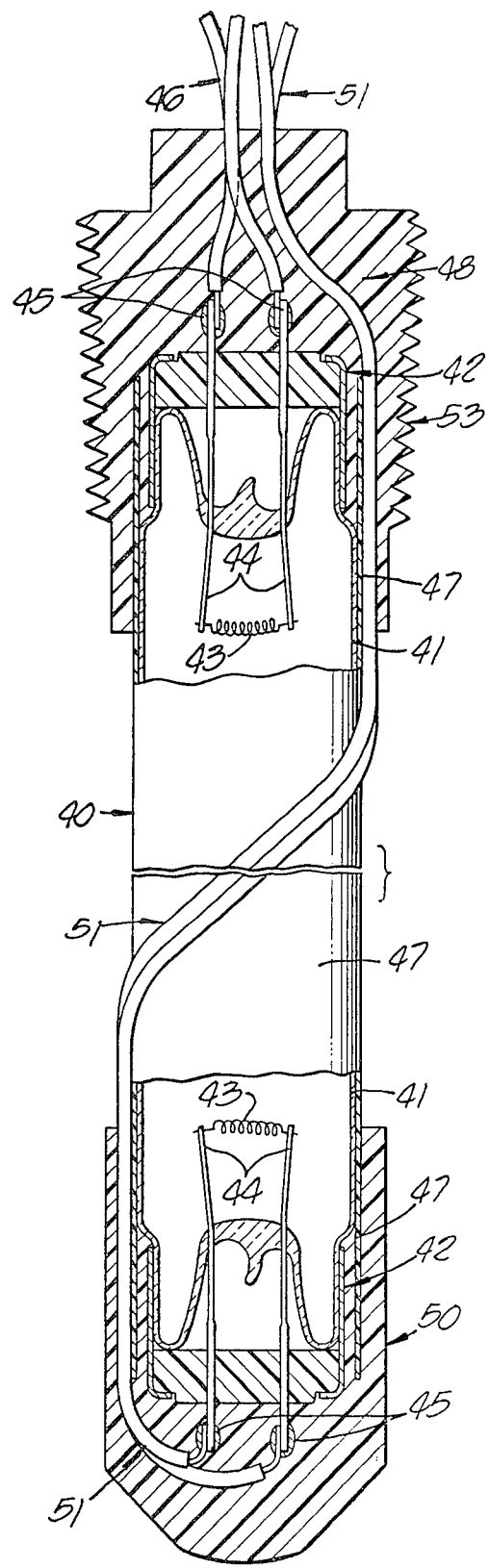

FLUID PURIFICATION DEVICE AND ULTRAVIOLET LAMP THEREFOR

CROSS REFERENCE TO RELATED APPLICATION

This application is a continuation-in-part of my copending application Ser. No. 490,238, filed July 22, 1974, now U.S. Pat. No. 3,923,663.

BACKGROUND OF THE INVENTION

1. Field of the Invention

This invention relates broadly to devices for purifying water and other fluids and has particular reference to an improved removably mounted ultraviolet lamp assembly for such devices.

2. Description of the Prior Art

Purifying devices for water and other fluid have been known heretofore in which the fluid passes first through a filter to filter out any solids and then passes a source of ultraviolet rays effective to destroy microorganisms, spores, and the like, which pass through the filter. Generally, this is accomplished by passing the fluid over the envelope of an ultraviolet lamp or over a quartz jacket surrounding the lamp.

It is found that in such known devices, during operation of the lamp, calcium and other colloidal matter which passes through the filter tends to coat the lamp envelope or other transparent medium separating the fluid from the lamp, thus building up a scale or other contamination which reduces the intensity of the ultraviolet rays and therefore reduces the effectiveness of the lamp in destroying the microorganisms, etc. This attenuation of the ultraviolet transmission is not easily detected by inspection and therefore the device must be frequently disassembled and the ultraviolet lamp or quartz jacket cleaned to insure effective sterilization.

In some of the known devices, attempts have been made to maintain the efficiency by employing mechanical scrubbers or scrapers to periodically remove the accumulated scale and other contamination, but these add to the complexity and cost of the device and have not proved entirely satisfactory.

Until rather recently, these prior fluid purification devices have in general comprised separate units for first filtering and then sterilizing the fluids. Such units are relatively bulky, complicated and difficult to disassemble for cleaning, inspection and replacement of the ultraviolet lamps, filters and other components.

As will be observed from U.S. Pat. No. 3,551,091, the patentee, L. P. Veloz, attempted to overcome the disadvantages attending the use of separate filtering and sterilizing units by providing a combination water filter and sterilizer within a single housing, and wherein a removable filter surrounds an ultraviolet lamp which is shielded against the fluid pressure by means of a surrounding quartz tube. Thus, it appears that while the embodiment of this patent did produce a more compact and simplified device, it did not solve the problem of scale and contamination buildup which tended to reduce the irradiating efficiency of the device during use.

Other attempts were also made to improve fluid sterilizing units, as disclosed for example in U.S. Pat. No. 3,700,406 to A. Landry, by utilizing fluorinated ethylene propylene plastic, commercially known as Teflon F.E.P., and which has excellent non-stick qualities, is non-contaminating, and will not deteriorate in the presence of ultraviolet light. In this patent it has been proposed to use such material for piping to carry the fluid past a source of ultraviolet light. However, attempts to utilize such material for piping has, in the main, been unsuccessful because of its high imperviousness to ultraviolet rays, when of sufficient thickness to withstand the normally used fluid pressures. For example, considering quartz to have an ultraviolet ray transmission factor of 100%, a sheet or the like of Teflon F.E.P. 0.010 inches thick will reduce U.V. transmission to 25%, although a sheet of Teflon F.E.P. 0.002 inches thick will transmit 75%. It will therefore be apparent that such material could not be used as piping or other means for conveying fluids under the pressures usually employed in connection with fluid purification systems, since it would require a thickness such that ultraviolet transmission would be unduly attenuated.

In its broad aspects, the present invention overcomes the above noted problems and disadvantages of the prior art devices by utilizing a unique ultraviolet lamp, the outer surface of which is covered with a thin film of a material having non-stick characteristics with respect to the fluid being treated, such as fluorinated ethylene propylene. The film is of such thinness as to have a high degree of transmission for the ultraviolet rays, and yet will withstand the fluid pressure in an associated flow channel because of its intimate engagement with the outer surface of the ultraviolet lamp envelope. With this arrangement scale and contamination around the lamp are substantially reduced, and efficiency of operation maintained over long periods of use.

SUMMARY OF THE INVENTION

The present invention provides an improved elongate ultraviolet lamp assembly which finds particular use in fluid purifying apparatus, the lamp having an extremely thin film of hermetically sealed fluorinated ethylene propylene or other suitable material intimately engaged with the outer surface of the envelope of the lamp to prevent contamination and accumulation of scale or other impurities thereon and yet permit transmission of a relatively large amount of ultraviolet rays therethrough. The lamp assembly is arranged to be removably mounted directly in the flow path of the fluid being treated in the fluid purifying apparatus.

One object of the herein described invention is to provide an ultraviolet lamp assembly of the above type which is rugged, simple, compact, easy to disassemble and highly effective.

A further object is to provide an improved ultraviolet lamp assembly for use in a fluid purifying device, which obviates the need for frequent cleaning of an ultraviolet lamp or other ultraviolet transmission element over which the fluid to be sterilized flows.

Another object is to provide an ultraviolet lamp assembly with base supporting means which permits the lamp to be selectively removably mounted in a fluid purifying device in reversed longitudinally extending positions to meet different installation requirements of the device.

Still another object is to provide an improved ultraviolet lamp assembly having a unique base supporting means which permits the lamp to be supported in a resilient non-rigid manner in an associated fixed housing, thus eliminating the need for precise construction tolerances in order to obtain perfect alignment of the lamp within the housing.

Yet another object is to provide an improved and unique ultraviolet lamp unit assembly as an article of manufacture for use in and as a replacement in a fluid purifying device.

Further objects and advantages of the invention will be brought out in the following part of the specification, wherein detailed description is for the purpose of fully disclosing several embodiments of the invention without placing limitations thereon.

BRIEF DESCRIPTION OF THE DRAWINGS

Referring to the accompanying drawings, which are for illustrative purposes only:

FIG. 3 is a sectional elevational view through another embodiment;

FIG. 4 is an enlarged longitudinal sectional view through an ultraviolet lamp assembly constructed according to one embodiment of the present invention.

DESCRIPTION OF THE EMBODIMENT SHOWN IN FIGS. 1, 2 AND 4

Figure 1:
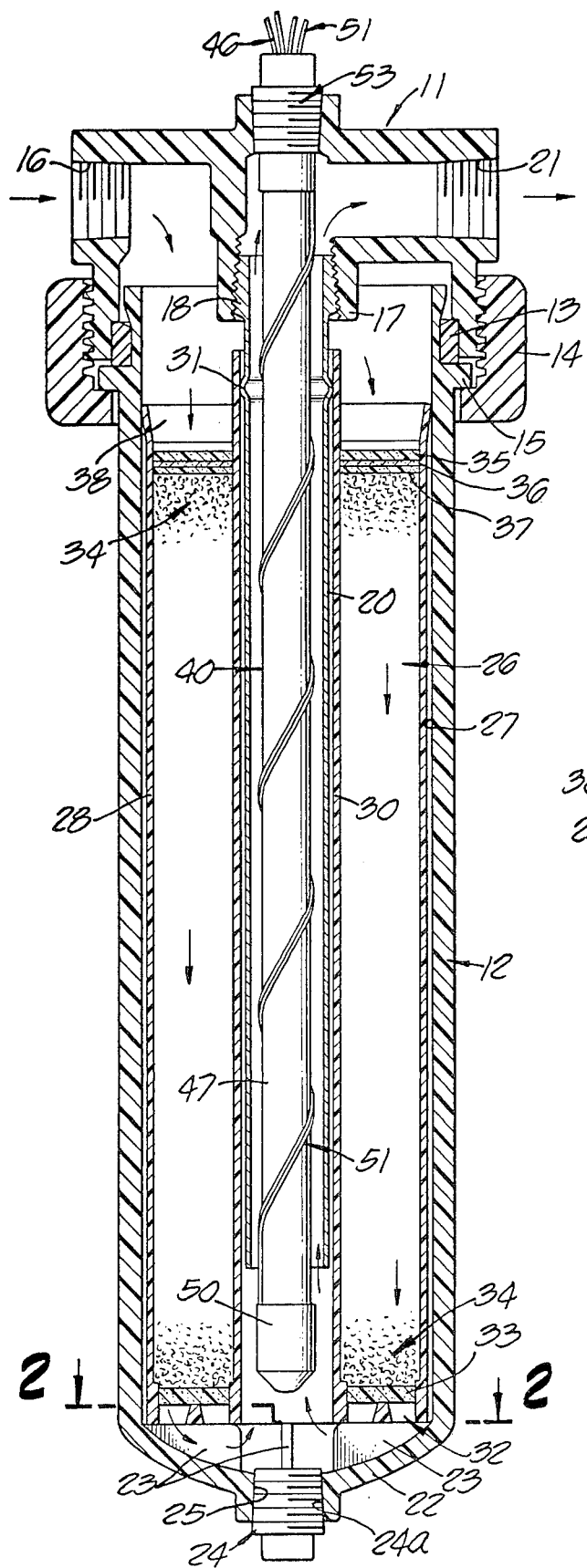
FIG. 1 is a sectional elevational view through one embodiment of a fluid purifying device embodying an ultraviolet lamp according to the present invention.
Figure 2:
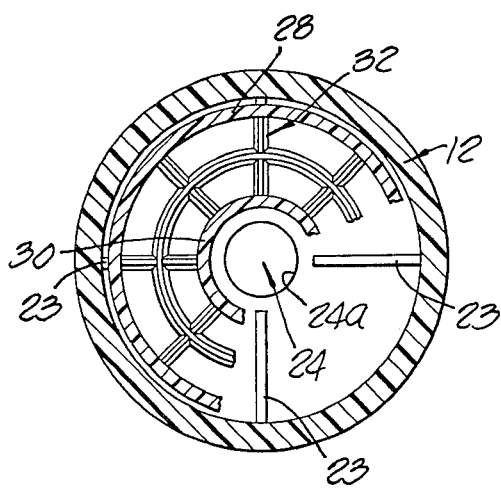
FIG. 2 is a fragmentary transverse sectional view taken substantially along the line 2—2 of FIG. 1.

Referring to FIGS. 1 and 2, the fluid purifying device shown therein comprises a two-part body including an upper housing part 11 and a lower housing part 12, both formed of a suitable plastic, such as polypropylene. An annular sealing ring 13 of elastomeric material is mounted between the housings 11 and 12 to seal the same against fluid pressure. A clamp nut 14 is screw threaded onto the housing part 11 and engages an annular flange 15 on housing part 12 to maintain the housing parts in assembled condition in which they cooperate to provide an interior chamber.

An inlet port 16 is formed in the upper housing 11 for connection to a source of fluid under pressure to be purified. Such inlet port directly communicates with the interior chamber of the body.

A hollow central boss 17 is formed on the upper housing 11 and is suitably connected as by a threaded connector 18 or other suitable means to a tube 20 of appropriate material and preferably of a material such as stainless steel or other highly reflective material with respect to ultraviolet rays. The interior of the tube 20 communicates with an outlet port 21 formed in the upper housing 11, through which the purified fluid is discharged.

A bottom wall 22 of the lower housing 12 is formed to provide a plurality of angularly spaced radially extending filter supporting fins 23 (see also FIG. 2) which surround a tapered drain plug 24 removably secured by screw threads 25 in a drain opening 24a in the bottom wall 22.

A tubular filter cartridge 26 is removably receivable within a bore 27 of the lower housing 12. This cartridge comprises a relatively thin flexible outer cylindrical envelope 28 of plastic or other suitable material and an inner coaxial central tube 30, also of plastic or other suitable material, and which loosely surrounds the reflector tube 20 and independently engages a circumferential bead 31 formed in the tube 20 adjacent its upper end. The envelope 28 and tube 30 are integrally connected at their lowermost ends to a perforated bottom wall structure 32 formed to provide a circular grating as best seen in FIG. 2. The wall 32 rests on the support fins 23 to provide an open communication between the lower end of the cartridge 26 and the interior of the reflector tube 20.

At the bottom of the filter cartridge 26, an annular filter disc 33 of suitable filter material fits within the filter element 28 and rests on the bottom wall 32 to support a filter body 34 of loose granular activated charcoal or other suitable filtering material.

At the top of the filter cartridge 26, a plurality of superimposed annular filter discs 35, 36 and 37 of porous or other suitable material are fitted within the filter envelope 28 to retain the filter material of the body 34. These discs may be formed with progressively finer degrees of porosity.

It should be noted that the upper end of the envelope 28 flares outwardly as indicated at 38 to peripherally engage the surface of the bore 27 of the housing 12. Thus, when a fluid pressure is applied to the upper end of the cartridge 26, the flared portion 38 will yield outwardly to form a seal, preventing the fluid from passing between the cartridge and the bore 27. On the other hand, when no fluid pressure is present, the cartridge 26 may be easily slid along the bore 27 for removal or replacement.

A high intensity ultraviolet lamp 40 (see also FIG. 4) is located in inwardly spaced relation within the reflector tube 20 and extends lengthwise therethrough. The lamp comprises an envelope 41 of quartz or other suitable material which is highly transparent to ultraviolet rays. This envelope is suitably bonded to cap elements 42 at its opposite ends. Ignition elements 43 are respectively supported by metal terminal posts 44 which are hermetically sealed within the cap elements 42. The terminal posts 44 at one end of the lamp are electrically connected at 45 to electric supply conductors 46, while the terminal posts 44 at the other end of the lamp are connected at 45 to electric supply conductors 51.

A unique feature of the lamp structure comprises the use of a thin sheath or film 47 of a material having a non-stick characteristic with respect to fluids being treated in the device, such as fluorinated ethylene propylene, for example, on the order of 0.002 inches or less in thickness, which is applied over and in intimate contact with the outer surface of the quartz envelope 41 and extends along the length thereof. A base assembly includes a plastic base member 48 molded over said one end portion of the lamp 40 and the film 47 to hermetically seal the same and the supply conductors 46 and 51 therein.

A cap 50, also of plastic, is molded over said other end of the lamp 40 and the film 47 to hermetically seal such parts and the connected ends of conductors 51 connected to the terminal posts 44 at this end. The conductors 51 are also covered with fluorinated ethylene propylene and are wrapped in a helical pattern around the film 47 along the length of the lamp 40.

The base member 48 is further provided on its outer surface with external tapered screw threads 53 whereby to removably mount the lamp in the upper housing 11 so as to extend within the reflector tube 20 and cooperate therewith to provide an annular fluid flow channel for irradiating fluid received from the upstream filter. Thus, the conductors 46 and 51 extend through the base member 48 for connection to a suitable source of electric current located exteriorly of the body.

From the above, it will be seen that the ultraviolet lamp assembly may be readily removed from the body without disassembling the latter. Further, the plug 24 and lamp base member 48 have similar tapered screw threads, and permit such elements to be interchanged so that the lamp assembly may be inserted and screwed into the bottom wall 22 of the housing 12, if so desired.

In operation, the fluid under pressure passes through the inlet port 16 and lengthwise through the filter cartridge 26. As it emerges through the bottom wall 32 of the cartridge, the filtered fluid is directed upwardly through a lower end portion of the cartridge tube 30 and thence through the reflector tube 20 and around the ultraviolet lamp assembly in an annular column where it is thoroughly exposed to ultraviolet irradiation. The conductors 51, due to their helically arranged pattern around the lamp, tend to impart a swirling motion to the fluid passing through the tube 20 to remove any particles which may tend to settle on the film covering 47. Finally, the sterilized fluid is discharged through the outlet port 21.

DESCRIPTION OF THE EMBODIMENT SHOWN IN FIG. 3

FIG. 3 illustrates an alternative form of fluid purifying device in which a different form of filter cartridge, as generally indicated at 55, is provided. The upper housing 11, lower housing 12, reflector tube 20 and ultraviolet lamp assembly 40 are, however, similar to those shown in FIGS. 1, 2 and 4 and are identified by the same reference numerals. In this case, the lamp assembly is illustrated as being mounted in the bottom wall 22 of the housing 12.

The cartridge 55 in this form of the invention comprises a perforated inner tube 56, preferably of plastic, on which is wound a suitable plastic filter filament to form an annular body 57. At the lowermost end of the housing 12, an annular filter retaining member 58 is secured by suitable adhesive or the like to the fins 23 and comprises a sharp upwardly facing annular ridge 60 and an inner tubular extension 61.

At the uppermost end of the housing 12, a second annular filter retaining member 62 having a downwardly facing sharp annular ridge 63 thereon is fitted over the adjacent end of the reflector tube 20 and is maintained in spaced relation with the boss 17 by a tubular spacer 64.

In assembling the filter cartridge 55, the upper housing 11 and attached reflector tube 20 are removed and the filter cartridge 55 inserted into the lower housing 12 over the tubular extension 61. The upper housing 11 is then replaced, and as the clamp nut 14 is actuated to draw the housings 11 and 12 together, the retainer members 58 and 62 embed their respective ridges 60 and 63 into the adjacent ends of the filter cartridge to hold the same in place and to prevent leakage of fluid around the ends of the cartridge.

In operation, fluid under pressure is directed through the inlet port 16, into the chamber surrounding the filter cartridge 55. Fluid then passes radially inwardly through the cartridge, including the perforated tube 56, and is guided downwardly along the outer surface of the tube 20 until it flows around the lower end of the reflector tube 20 and thence upwardly between the ultraviolet lamp assembly and reflector tube to the outlet port 21.

DESCRIPTION OF THE EMBODIMENT SHOWN IN FIG. 5

Figure 5:
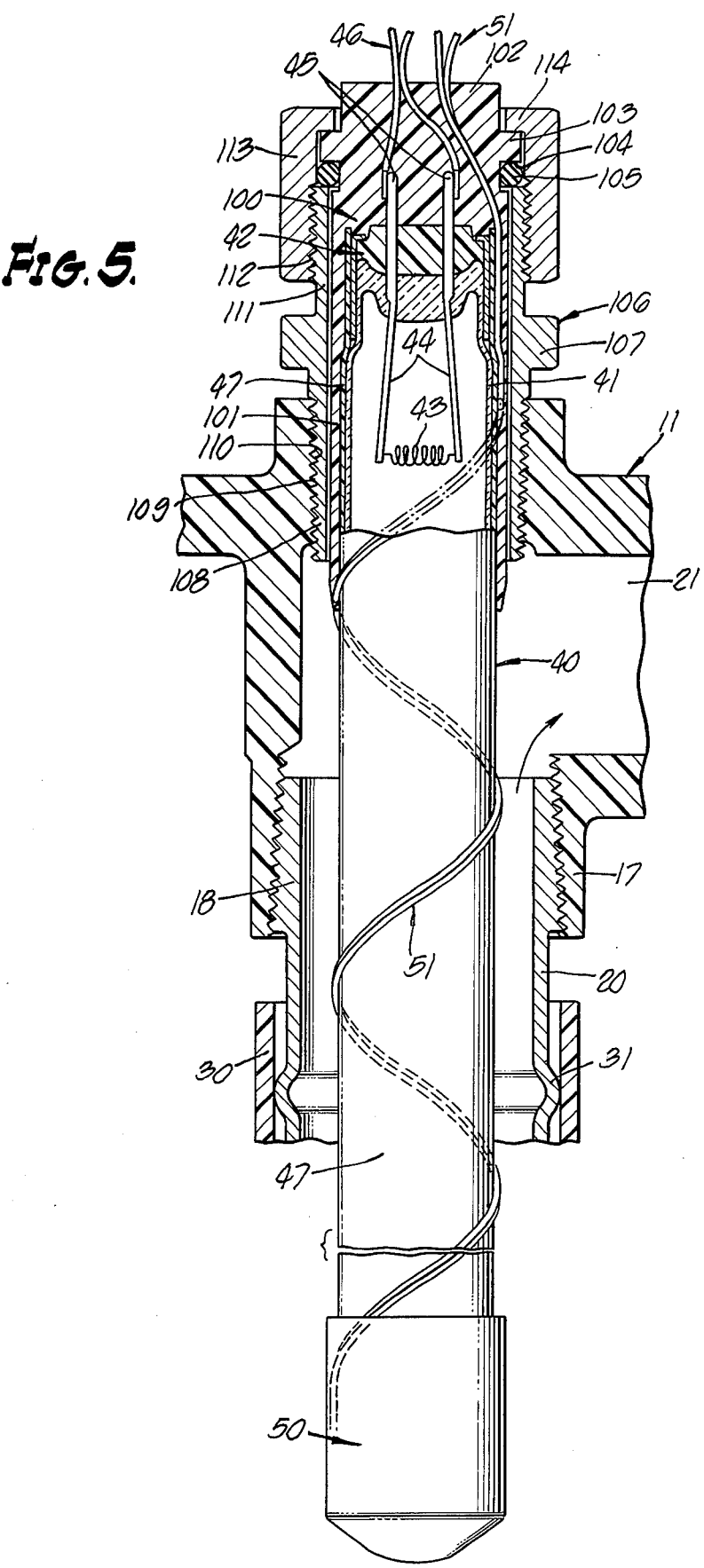
FIG. 5 is an enlarged longitudinal sectional view through yet another embodiment of the invention.

In FIG. 5, there is illustrated a modified form of the ultraviolet lamp structure 40 and the manner in which it is mounted in the associated housing of the fluid purification device, and wherein similar elements have been indicated by the same numerals. The structure of the ultraviolet lamp differs primarily from that shown in FIG. 4 in that the lamp construction at the base end and the manner of mounting the lamp in the associated housing of the fluid purification device have been modified so that the lamp will be resiliently mounted rather than rigidly mounted as in the previously described arrangement, and to provide a supporting structure which will enable the lamp to be more easily removed for replacement.

Referring more specifically to FIG. 5, it will be seen that instead of utilizing a plastic base member 48 which is permanently secured to this end of the lamp and provided with tapered screw threads for rigidly mounting the lamp in the housing of the fluid purification device, the modified structure utilizes a generally cylindrical plastic base member 100 which is molded over this end of the lamp and is formed with a tubular portion 101 at one end and a solid head portion 102 at its other end. The tubular portion extends over and is bonded to the adjacent end of the film 47 to hermetically seal the supply conductors 46 and 51 therein. The head portion 102 is provided with a circumferentially extending outwardly projecting abutment flange 103 which extends outwardly over an underlying circumferentially extending groove 104 to provide a seat for an O-ring seal 105.

The modified lamp embodiment is arranged to be removably mounted in the housing of the fluid purifying device, and for this purpose there is provided a double ended tubular bushing 106 having a uniform internal diameter. This bushing is formed intermediate its ends to provide a multi-sided surrounding flange 107 for reception of a wrench or other tool, when mounting the bushing.

One end of this bushing, as indicated by the numeral 108, is provided on its outer surface with external tapered screw threads 109, whereby the bushing may be permanently mounted in an internally threaded bore of the housing of the fluid purifying device with which the ultraviolet tube is to be utilized.

The other end of this bushing, as indicated by the numeral 111 is provided with external threads 112 of uniform diameter for threaded connection with the internal threads of a clamping nut 113 which is formed at its outermost end with an inwardly extending annular abutment flange 114 which is adapted to overlie the abutment flange 103 of an associated modified form of the ultraviolet tube as shown in FIG. 5, when the tube is positioned in the housing 106.

It is a feature of the modified ultraviolet tube structure that the tubular portion 101 of the base member is of a length such that it will extend beyond the end 108 of the mounting bushing 106, when the tube is in a mounted position therein. Also, it will be noted that there is a circumferential clearance space between the outer surface of the tubular portion 101 and the inner surface of the bore of the bushing. It will thus be apparent that when the clamping nut 113 is tightened, it will force the O-ring seal 105 into a sealing position against the end surface of the end 111 of the bushing. Also, in this arrangement the O-ring 105 provides a resilient rather than a rigid support for the lamp and properly aligns the lamp within the associated fluid purification device and eliminates the necessity of precise construction tolerances in order to obtain a proper alignment of the lamp. Removal of the modified ultraviolet lamp is a simple procedure, since it is only necessary to remove the clamping nut 113, whereupon the lamp is easily withdrawn from the bushing, which remains permanently connected with the housing of the purification device.

From the foregoing description and drawings, it will be clearly evident that the delineated objects and features of the invention will be accomplished.

Various modifications may suggest themselves to those skilled in the art without departing from the spirit of the invention and, hence, it is not wished to be restricted to the specific forms shown or uses mentioned, except to the extent indicated in the appended claims.

I claim:

1. An ultraviolet lamp for immersion in the fluid of a fluid purifying device, and the like, comprising: an elongate transparent envelope having sealed opposite ends, each mounting an ignition element located within said envelope; a continuous solid thin film of material having a non-stick characteristic with respect to a fluid being treated by the device, said film surrounding said envelope and being fixed to and in intimate contact with the outer surface of said envelope; base means at one end of said envelope including a base member hermetically sealing the adjacent end of said film with respect to said envelope; and a cap member for the opposite end of said envelope hermetically sealing the adjacent end of said film with respect to said envelope.

2. An ultraviolet lamp according to claim 1, wherein said base means further includes electric connection conductors for said ignition elements and externally threaded means for providing a mounting screw plug.

3. An ultraviolet lamp according to claim 2, wherein the externally threaded means includes external, tapered screw threads formed on an outer surface of said base member.

4. An ultraviolet lamp according to claim 2, wherein connection conductors to the cap end of said lamp extend in a helical manner around said film, said conductors having an insulating film of fluorinated ethylene propylene.

5. An ultraviolet lamp according to claim 1, wherein the base member includes a circumferentially extending abutment flange at the outer end of the base member.

6. An ultraviolet lamp according to claim 5, further including a sealing ring disposed on the base member in underlying relation to said abutment flange.

7. An ultraviolet lamp according to claim 5, wherein the base means further includes a bushing removably surrounding said base member, said bushing having external threads at one end for threadingly engaging with a supporting structure, and threads at the other end of said bushing; a clamping nut having threads for engaging the threads at said other end of the bushing, and an internal flange for engaging the abutment flange of said base member and being operable upon the tightening of said clamping nut to clampingly secure the bushing and the base member together.

8. An ultraviolet lamp according to claim 7, further including a sealing ring positioned between the abutment flange and the adjacent end of the bushing to provide a resilient seal between the abutment flange and the bushing, and to further provide a resilient non-rigid support for the lamp.

9. An ultraviolet lamp according to claim 8, wherein the base means further includes electric connection conductors for the ignition elements, the connectors being embedded in the base member.

10. An ultraviolet lamp unit according to claim 9, wherein connection conductors to the cap end of said lamp extend in a helical manner around said film, said conductors having an insulating film of fluorinated ethylene propylene.

* * * * *

UNITED STATES PATENT AND TRADEMARK OFFICE
CERTIFICATE OF CORRECTION

PATENT NO. : 4,101,777
DATED : July 18, 1978
INVENTOR(S) : WILLIAM P. REID

It is certified that error appears in the above—identified patent and that said Letters Patent are hereby corrected as shown below:

Column 6, line 56, "housing" should read --bushing--.

Signed and Sealed this

Sixteenth Day of January 1979

[SEAL]

Attest:

RUTH C. MASON
Attesting Officer

DONALD W. BANNER
Commissioner of Patents and Trademarks